United States Patent [19]

Gane et al.

[11] 4,319,056
[45] Mar. 9, 1982

[54] PROCESS FOR THE HYDROCARBONYLATION OF METHANOL TO ETHANOL IN THE PRESENCE OF AN INERT LIQUID

[75] Inventors: Brian R. Gane, Weybridge; David G. Stewart, Epsom, both of England

[73] Assignee: The British Petroleum Company Limited, London, England

[21] Appl. No.: 113,614

[22] Filed: Jan. 21, 1980

Related U.S. Application Data

[63] Continuation of Ser. No. 957,700, Nov. 6, 1978, abandoned.

[30] Foreign Application Priority Data

Nov. 8, 1977 [GB] United Kingdom ............... 46329/77

[51] Int. Cl.$^3$ ....................... C07C 29/32; C07C 29/36
[52] U.S. Cl. .................................................... 568/902
[58] Field of Search ........................................ 568/902

[56] References Cited

U.S. PATENT DOCUMENTS

| | | | |
|---|---|---|---|
| 3,248,432 | 4/1966 | Riley et al. | 568/902 |
| 4,045,492 | 8/1977 | Kniese et al. | 568/902 |
| 4,133,966 | 1/1979 | Pretzer et al. | 568/902 |

*Primary Examiner*—Joseph E. Evans
*Attorney, Agent, or Firm*—Brooks, Haidt, Haffner & Delahunty

[57] ABSTRACT

Ethanol is produced by reacting methanol with hydrogen and carbon monoxide at elevated temperature and pressure in the presence of a catalyst comprising cobalt, and iodide or a bromide and a compound having X(A)(B)(C) in which formula X is a nitrogen or phosphorus and A, B and C are individually monovalent organic radicals, or X is phosphorus and any two of A,B and C together form an organic divalent cyclic ring system bonded to the X atom, or X is nitrogen and all of A,B and C form an organic trivalent cyclic ring system bonded to the X atom, and in the additional presence of an added inert liquid which is characterized as a compound capable of forming, under normal conditions of temperature and pressure, a separate phase in the presence of methanol containing up to 20% w/w water, which compound contains in its structure bonds other than carbon/carbon and carbon/hydrogen. Typical of the inert liquids which may be employed are chlorobenzene, decanoic acid, polydimethylsiloxane fluid and methyl phenyl silicone fluid. The addition of the inert liquid suppresses side-reactions and thereby increases the total yield and selectivity to ethanol.

11 Claims, No Drawings

PROCESS FOR THE HYDROCARBONYLATION OF METHANOL TO ETHANOL IN THE PRESENCE OF AN INERT LIQUID

This is a continuation of application Ser. No. 957,700, filed Nov. 6, 1978, now abandoned.

The present invention relates to the production of ethanol from methanol and synthesis gas (mixtures of carbon monoxide and hydrogen) in the presence of a cobalt-containing catalyst.

Ethanol is a valuable industrial product which is generally manufactured either by fermentation of natural products eg molasses or by hydration of ethylene in the presence of an acid catalyst, such as phosphoric acid. The rapidly dwindling reserves of crude oil from which ethylene is derived and the associated need to utilise fully the remaining natural resources such as coal and the vast amounts of gases eg methane potentially available from the exploitation of North Sea oilfields has stimulated researchers to investigate other routes to ethanol utilising these materials as feedstocks. Both coal and methane gas can be converted into synthesis gas ($CO+H_2$), which in turn can be reacted to form methanol, which methanol can be further reacted with carbon monoxide and hydrogen under appropriate conditions to form ethanol.

It has long been known that methanol can be hydrocarbonylated with hydrogen and carbon monoxide to ethanol in the presence of a water soluble cobalt catalyst at high temperatures and pressures. The course of this reaction can be represented by the following equation:

$$CH_3OH + CO + 2H_2 \rightarrow C_2H_5OH + H_2O$$

The problem with the majority of prior art processes is that they produce large amounts of by-products such as esters, and acids in addition to ethanol. Our copending application Ser. No. 908,060 filed May 22, 1978 which was abandoned in favor of continuation application Ser. No. 52,006 filed on June 25, 1979, now abandoned, describes one method of suppressing or inhibiting undesirable by-product formation and thereby increasing the total realisable yield and selectivity to ethanol, which method involves the addition of acids and/or acid derivatives to the reaction catalysed by cobalt optionally in the presence of either a halide or an organo-phosphorus compound as a promoter. Another method whereby ethanol is produced in higher yield and greater selectivity by reacting methanol, carbon monoxide and hydrogen in the presence of a nonpolar solvent and a catalyst comprising a tertiary phosphine, cobalt and iodine or bromine is described in U.S. patent application Ser. No. 585,276 (Shell, now abandoned). Two elements are said to be essential in the process of the invention; (a) a nonpolar solvent and (b) a catalyst comprising a tertiary phosphine, cobalt and an iodine or bromide. The nonpolar solvent is selected from the group consisting of alkanes, benzene and alkyl-substituted benzenes. None of the solvents listed in the specification contains bonds other than carbon/carbon and carbon/hydrogen in their molecular structure, ie they are all hydrocarbons.

We have found that, in the hydrocarbonylation of methanol with hydrogen and carbon monoxide to ethanol in the presence of a catalyst comprising both an iodide or a bromide and either an organo-phosphorus or organo-nitrogen compound at high temperatures and pressures, the total realisable yield and selectivity to ethanol may be increased by the addition of an inert liquid.

The term, inert liquid, as used in this specification means a compound which does not poison or otherwise adversely affect the catalyst, is mainly in liquid form under the conditions of the reaction, is capable of forming a separate phase in the presence of methanol containing up to 20% w/w water under normal conditions of temperature and pressure and is further characterised by having in its molecular structure one or more atoms other than carbon and hydrogen. The inert liquid typically contains such bonds as carbon/oxygen, carbon/sulphur, carbon/halogen, carbon/nitrogen, or carbon/silicon as well as normal carbon/carbon and carbon/hydrogen bonds.

By total realisable yield of ethanol within the context of the specification is meant the yield of free ethanol plus the yield of ethanol realisable by the hydrolysis of ethanol-yielding esters (eg ethyl acetate). In the same way, by realisable methanol is meant the free methanol plus the methanol realisable by the hydrolysis of methanol-yielding esters (eg methyl acetate). Thus, % Molar Yield of Realisable Ethanol =
$$\frac{\text{Moles of realisable methanol converted into realisable ethanol} \times 100}{\text{Total moles of realisable methanol fed}}$$

and,

% Molar Selectivity to Realisable Ethanol =
$$\frac{\text{Moles of realisable methanol converted into realisable ethanol} \times 100}{\text{Total moles of realisable methanol converted}}$$

By the yield of realisable acetic acid is meant the yield of free acetic acid plus the yield of acetic acid realisable by the hydrolysis of acetic acid-yielding esters (eg methyl acetate). In calculating the yield it is assumed that all the acetic acid is derived from methanol and synthesis gas and no account is taken of acetic acid derived from cobalt acetate, when this is added as catalyst. Thus, % Molar Yield of Realisable Acetic Acid =
$$\frac{\text{Moles of realisable methanol converted into realisable acetic acid} \times 100}{\text{Total moles of realisable methanol fed}}$$

% Methanol conversion =
$$\frac{\text{Total moles of methanol converted}}{\text{Total moles of methanol fed}} \times 100$$

Thus according to the present invention there is provided a process for the production of ethanol which process comprises reacting at elevated temperature and pressure methanol with hydrogen and carbon monoxide in the presence of an inert liquid, as hereinbefore defined, and a catalyst comprising cobalt, an iodide or a bromide and a compound having the formula:

$$X{\begin{matrix}\nearrow A \\ -B \\ \searrow C\end{matrix}} \qquad (I)$$

wherein X is nitrogen or phosphorus and A, B and C are individually monovalent organic radicals, or X is phosphorus and any two of A, B and C together form an organic divalent cyclic ring system bonded to the X atom, or X is nitrogen and all of A, B and C together form an organic trivalent cyclic ring system bonded to the X atom.

Methanol is a readily available industrial product. It is generally manufactured on an industrial scale from synthesis gas. Whilst it is preferred that the methanol be substantially pure the presence of small amounts of certain impurities can be tolerated. The methanol may however contain up to 50% by weight of water.

Mixtures of the gases hydrogen and carbon monoxide are abundantly available in the form of synthesis gas. Methods for preparing synthesis gas are well-known in the art and usually involve the partial oxidation of a carbonaceous substance, eg coal. Alternatively synthesis gas may be prepared, for example, by thermal steam reforming of methane. For the purpose of the present invention the molar ratio of carbon monoxide to hydrogen may suitably be in the range 2:1 to 1:3, preferably 1:1 to 1:2. Methods for adjusting the molar ratio of carbon monoxide to hydrogen are well-known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

Compounds capable of forming, under normal conditions of temperature and pressure, a separate phase in the presence of methanol containing up to 20% w/w water fall into a class characterised by the presence of bonds other than carbon/carbon and carbon/hydrogen, eg carbon/oxygen, carbon/sulphur, carbon/halogen, carbon/nitrogen or carbon/silicon. Thus the compound may be, for example, an aryl halide, an ether, a thiophene, a long chain acid, an aromatic acid or a silicone oil. An example of a suitable aryl halide is chlorobenzene. A suitable example of a long chain acid is decanoic acid. Typical of the silicone oils which may be used are polydimethylsiloxane fluids and methyl phenyl silicone fluids. Specific fluids which have been found useful in the process are the DC 200 series of fluids supplied by Dow Corning. Those compounds that are capable of forming, under normal conditions of temperature and pressure, a separate phase in the presence of methanol containing up to 20% w/w water but otherwise poison or adversely affect the catalyst (ie, non-inert compounds) are not included within the scope of the present invention.

The catalyst comprises cobalt, an iodide or bromide and a compound having the formula (I). Any source of cobalt which will react with carbon monoxide to yield a cobalt carbonyl or hydro carbonyl cobalt complex can be used in the process of the present invention. Cobalt is preferably employed in the ionic form, but the use of cobalt metal to react in situ to form ionic cobalt which then further reacts to form the desired cobalt complex is within the scope of the present invention. Typical sources of cobalt are, for example, compounds such as cobalt acetate, cobalt formate, cobalt propionate and the like, which under the reaction conditions form carbonyl or carbonyl/hydride complexes. The iodide or bromide can be added either in ionic form, eg as cobalt iodide or cobalt bromide, or as molecular iodine ($I_2$) or bromine ($Br_2$). Furthermore the iodide may be added as an alkyl or aryl iodide or bromide, preferably methyl iodide. However, the iodide or bromide may also be added in ionic form utilising cations which are inert with regard to the hydrocarbonylation reaction. Typical of the inert form is potassium iodide or bromide, sodium iodide or bromide and lithium iodide or bromide.

Compounds having the formula (I) are tertiary phosphines, amines, and nitrogen-containing heterocyclic systems, of which phosphines are preferred. A class of phosphines found to be particularly useful in the process of the present invention are those disclosed by Dewhirst in U.S. Pat. No. 3,759,838. These compounds are phosphines having the general formula:

$$R_3P \qquad (II)$$

wherein R independently is an organo group containing from 1 to 20 carbon atoms, is preferably free from aliphatic carbon-carbon unsaturation, and is bonded to the phosphorus atom by a carbon/phosphorus bond. The organo group R in the phosphine of formula (II) is preferably a hydrocarbyl group which may be a saturated aliphatic, a saturated cycloaliphatic, an aromatic, a substituted saturated aliphatic, a substituted saturated cycloaliphatic or a substituted aromatic group of which the unsubstituted saturated and aromatic groups are preferred. The substituents are preferably free from aliphatic carbon-carbon unsaturation and may contain, besides atoms of carbon and hydrogen, other atoms, such as oxygen, sulphur and halogen, in particular halogen of atomic number from 9 to 35, provided that such atoms are not directly bonded to phosphorus. Illustrative of suitable saturated aliphatic R groups are hydrocarbyl R groups such as methyl, ethyl, propyl, isopropyl, butyl, isoctyl, decyl, dodecyl, octadecyl, cyclohexyl, cyclopentyl, 3,4-dimethyl cyclopentyl, cyclooctyl, benzyl and β-phenylethyl. Aromatic R groups include hydrocarbyl aromatic groups such as phenyl, tolyl, xylyl, p-ethylphenyl, p-tert-butylphenyl, m-octylphenyl, 2,4-diethylphenyl, p-phenylphenyl, m-benzylphenyl and 2,4,6-trimethylphenyl. In the compound of formula (II) the R moieties may be the same or different, although for economic reasons they are preferably identical. Exemplary compounds of formula (II) are triethyl phosphine, tributylphosphine, tricyclohexylphosphine, triphenylphosphine, tris(4-tolyl)phosphine, tris(3-chlorophenyl)phosphine, diphenylhexylphosphine, dibutyloctadecylphosphine, tribenzylphosphine, cyclohexyldibutylphosphine and the like. Preferred compounds are triethylphosphine, tri-n-butylphosphine, tricyclohexylphosphine, tri-t-butylphosphine and triphenylphosphine.

Another type of phosphine which may be used in the operation of the invention is that disclosed by Mason et al in U.S. Pat. No. 3,400,163. These compounds are bicyclic heterocyclic tertiary phosphines, and are generally hydrocarbyl-substituted or unsubstituted monophosphabicyclo-alkanes of 8 to 9 atoms in which the smallest phosphorus-containing ring contains at least 5 atoms and the phosphorus atom therein is a member of a bridge linkage but is not a bridgehead atom.

Exemplary compounds of formula (I) wherein X is nitrogen are pyridine, diphenylamine and triphenylamine.

The term "hydrocarbyl" has been used throughout the foregoing in its accepted meaning as representing a radical formed from a hydrocarbon by removal of a hydrogen atom.

The exact nature of the catalysts of this invention under the reaction conditions is not known but they are thought to be phosphine or nitrogen-containing ligand-/cobalt carbonyl/hydride/halide complexes. The cobalt is thought to be in a reduced state but its exact valency is not known. The catalyst may be prepared by first reacting the individual components together and then adding the mixture to the reaction vessel, or by adding the individual components to the reaction vessel and allowing the catalyst to form under the reaction conditions.

In addition to the inert liquid essential to the invention there may also be added nonpolar solvents such as alkanes, benzene and alkyl-substituted benzenes.

Methanol may suitably be reacted with carbon monoxide and hydrogen at any temperature in the range 150 to 250, preferably 180° to 230° C. and at a pressure greater than 100 bars, preferably in the range 140 to 300 bars.

The process may be carried out batchwise or continuously, operation in a continuous manner being preferred. The process may be carried out continuously for example by continuously feeding methanol and synthesis gas to a reactor containing the catalyst and the inert liquid, removing from the reactor a liquid product containing ethanol, by-products, unchanged methanol, catalyst and unreacted synthesis gas, separating the synthesis gas which may be recycled to the reactor, removing light ends including ethers, separating the product containing ethanol and by-products from the catalyst and thereafter recovering ethanol from the by-products, there being recycled to the reactor the catalyst, methanol and inert liquid. Other reaction by-products particularly those which can act as precursors for the formation of ethanol such as acetaldehyde and 1,1-dimethoxyethane may also be recycled to the reactor with advantage. It may be necessary to feed from time to time further catalyst.

The residence time may suitably be up to 8 hours, but is preferably in the range of from 10 to 180 minutes. Within the context of the specification the residence time for batchwise operation is that time during which the reactor is at the specified reaction temperature. When the process is operated continuously the residence time is calculated as follows:

Residence Times (Hours) =
$$\frac{\text{Volume of the reactor occupied by the liquid phase at STP (liters)}}{\text{Total flow of liquid into the reactor (liters/hour at STP)}}$$

With regard to the various ratios of reactants to be employed in the process of the invention it has already been stated that the methanol may contain up to 50% by weight of water. In certain circumstances the addition of water may be beneficial to the reaction, ie the ratio of methanol to water in the feed can be adjusted so that two phases are present either at the start or at the end of the reaction or both. The molar ratio of methanol to inert liquid can be varied within wide limits, eg from 30:1 to 1:10, preferably from 25:1 to 1:2. In the case of silicone oils for which the molecular weight is not known with any degree of certainty the volume added/volume of methanol may be in the range of 0.05:50, preferably from 0.1 to 5 v/v. In both continuous and batch operations the molar ratio of methanol to synthesis gas fed may be in the range of from 10:1 to 1:20, preferably from 2:1 to 1:5.

In the catalyst the molar ratio of cobalt to iodine or bromine, may be in the range from 1:3 to 10:1, preferably from 1:1 to 5:1. The molar ratio of cobalt to compound of formula (I) may be in the range of from 2:1 to 1:10, preferably from 1:1 to 1:5. The molar ratio of iodine or bromine to compound of formula (I) may be in the range of from 2:1 to 1:10 preferably from 1:1 to 1:8. The molar ratio of cobalt to methanol may be in the range of from 1:10 to 1:1,000, preferably from 1:40 to 1:800.

When the inert liquid is not itself a long-chain acid or an aromatic acid there may be added to the reaction mixture an acid and/or an acid derivative thereof having the formula:

wherein the substituent R is a hydrocarbyl group or an oxygen-containing hydrocarbyl group and the substitutent X is the group $-OR^1$ in which $R^1$ is independently a hydrogen atom, a hydrocarbyl group or an oxygen-containing hydrocarbyl group or X is the group $-O-CO-R^2$ wherein $R^2$ is independently a hydrocarbyl group or an oxygen-containing hydrocarbyl group, as described in our copending application No. 22490/77. Preferred compounds having the structural formula (III) are acetic acid and methyl acetate. The acid and/or acid derivative of structural formula (III) may be added in an amount such that the molar ratio of acid and/or acid derivative to free methanol can be as high as 1.5:1, more usually in the range of from 0.1:1 to 0.7:1.

The invention will now be illustrated by reference to the following Examples.

EFFECT OF DIFFERENT TYPES OF INERT LIQUID

Example 1

A stainless steel, magnetically-stirred autoclave equipped for pressurised reactions was charged under nitrogen with methanol (0.68 mole) containing cobalt acetate tetrahydrate (0.0084 mole), iodine (0.0042 mole) and tri-n-butylphosphine (0.0147 mole). To this mixture was further added 55 mls silicone oil (Silicone Fluid Type DC 200/100 cS supplied by Dow-Corning Ltd). The system was purged with nitrogen, then pressurised to 200 bars with a mixture of carbon monoxide and hydrogen (1:1 molar). The reactor temperature was then raised to 205° C. and maintained at this temperature for 2 hours. When heating was started the pressure in the reactor rose above 200 bars and then began to decrease as the reaction commenced. During the course of the reaction, whenever the pressure in the autoclave fell to 140 bars a fresh charge of carbon monoxide and hydrogen (1:1 molar mixture) was added thereby increasing the reactor pressure to 200 bars. After two hours at 205° C. the autoclave was allowed to cool and the reaction product was analysed. Two liquid phases were noted at STP both before and after the reaction. The feed composition is given in Table 1A and the results are given in the following Table 1B.

Comparison Test A

The procedure described in Example 1 was followed using the reactants in the concentrations shown in Table 1A and with the results shown in Table 1B.

This is not an example according to the present invention because no inert liquid capable of forming, under normal conditions of temperature and pressure, a separate phase in the presence of methanol containing up to 20% w/w water was added. A single liquid phase at STP was noted both before and after the reaction.

Example 2

The procedure of Example 1 was repeated except that chlorobenzene was added to the methanol, cobalt acetate tetrahydrate, iodine, tri-n-butylphosphine mixture in place of silicone oil. A single phase at STP was noted before the reaction and two phases at STP were observed after the reaction.

The feed composition is given in Table 1A and the results are given in Table 1B.

Example 3

The procedure of Example 1 was followed except that the silicone oil in the reaction mixture was replaced by tetrahydrothiophen. A single phase was observed before and two phases were observed at STP after the reaction.

The feed composition is given in Table 1A and the results are given in Table 1B.

Example 4

The procedure of Example 1 was followed except that the silicone oil in the reaction mixture was replaced by diphenyl ether. Two phases were observed at STP both before and after the reaction.

The feed composition is given in Table 1A and the results are given in Table 1B.

Example 5

The procedure of Example 1 was repeated except that chlorobenzene (0.63 moles) and deionised water (0.47 moles) were added to the methanol, cobalt acetate tetrahydrate, iodine, tri-n-butylphosphine mixture in place of silicone oil. Two phases were noted at STP both before and after the reaction.

The feed composition is given in Table 1A and the results are given in Table 1B.

Comparison Test B

The procedure described in Example 1 was followed except that tributyl phosphine in the reaction mixture was replaced by tricyclohexylphosphine and no inert liquid was added. A single phase was observed at STP both before and after the reaction. The feed composition is given in Table 1A and the results are given in Table 1B.

This is not an example according to the present invention because no inert liquid capable of forming, under normal conditions of temperature and pressure, a separate phase in the presence of methanol containing up to 20% w/w water was added.

Example 6

The procedure of Example 1 was repeated except that the silicone oil in the reaction mixture was replaced by decanoic acid and the tri-n-butylphosphine was replaced by tricyclohexylphosphine. Furthermore the experiment was carried out on a larger scale. Two phases were noted at STP both before and after the reaction.

The feed composition is given in Table 1A and the results are given in Table 1B.

EFFECT OF VARYING THE AMOUNT OF INERT LIQUID ADDED

Example 7

The procedure of Example 1 was repeated except that chlorobenzene was added to the methanol, cobalt acetate tetrahydrate, iodine, tri-n-butylphosphine mixture in place of silicone oil. A smaller amount of chlorobenzene (0.13 moles) was added in this Example than in Example 2 (0.63 moles). A single phase was noted at STP both before and after the reaction.

The feed composition is given in Table 2A and the results are given in Table 2B.

Example 8

Example 7 was repeated except that the amount of chlorobenzene was reduced from 0.13 moles to 0.072 moles. A single phase was observed at STP both before and after the reaction.

The feed composition is given in Table 2A and the results are given in Table 2B.

Example 9

Example 1 was repeated except that the volume of silicone oil added was reduced from 55 mls to 7.3 mls. The feed composition is given in Table 2A and the results are given in Table 2B.

EFFECT OF VARYING THE AMOUNT OF TRI-ALKYLPHOSPHINE

Example 10

The procedure of Example 1 was repeated except that chlorobenzene was added to a methanol, cobalt acetate tetrahydrate, iodine, tri-n-butylphosphine mixture. A smaller amount of tri-n-butylphosphine (0.009 moles) was added in this Example than in Example 2 (0.0175 moles). A single phase was observed before and two phases were observed at STP after the reaction.

The feed composition is given in Table 3A and the results are given in Table 3B.

Example 11

Example 10 was repeated on a larger scale. The molar ratio of cobalt acetate tetrahydrate to tri-n-butylphosphine was reduced from 1:0.89 to 1:0.5. The feed composition shown in Table 3A and the results obtained are shown in Table 3B. A single phase was observed before reaction and two phases were observed at STP after reaction.

Comparison Test C

The procedure of Example 1 was followed except that chlorobenzene was added to a methanol, cobalt acetate, tetrahydrate, iodine mixture. There was observed a single phase before reaction and two phases at STP after the reaction. The feed composition is given in Table 3A and the results are given in Table 3B.

This is not an example according to the present invention because no compound of formula I was present in the reaction mixture.

EFFECT OF VARYING THE NATURE OF THE COMPOUND OF FORMULA I

Example 12

The procedure of Example 8 was followed except tributylphosphine was replaced by triphenylphosphine.

A single phase was observed at STP both before and after the reaction.

The feed composition is given in Table 4A and the results are given in Table 4B.

Example 13

Example 8 was repeated except tributylphosphine was replaced by triphenylamine. A single phase was observed before and two phases at STP after, the reaction. The feed composition is given in Table 4A and the results are given in Table 4B.

Example 14

The procedure of Example 2 was followed except that tributylphosphine was replaced by triphenylphosphine. Before reaction a single phase was observed at STP and after reaction two phases were noted at STP. The feed composition is given in Table 4A and the results are given in Table 4B.

Example 15

Example 14 was repeated except that the triphenylphosphine was replaced by tricyclohexylphosphine. A single phase was observed before, and two phases at STP after, the reaction. The feed composition is given in Table 4A and the results obtained are given in Table 4B.

EFFECT OF ADDING COMPOUNDS ADDITIONAL TO THE INERT LIQUID

Example 16

The procedure of Example 1 was followed except that the silicone oil in the reaction mixture was replaced by a small amount of chlorobenzene. In addition methyl acetate was added to the reactor feed. A single phase was observed at STP both before and after the reaction.

The feed composition is given in Table 5A and the results are given in Table 5B.

EFFECT OF VARYING THE MOLAR RATIO OF CARBON MONOXIDE TO HYDROGEN

Example 17

A stainless steel, magnetically-stirred autoclave equipped for pressurised reactions was charged under nitrogen with methanol (1.80 mole) containing cobalt acetate tetrahydrate (0.0225 mole), iodine (0.0113 mole) and triphenyl phosphine (0.0393 mole). To this mixture was further added chlorobenzene (0.072 mole). The system was purged with nitrogen, then pressurised to 120 bars (roughly equivalent to a pressure of 200 bars at 195° C.) with a mixture of carbon monoxide and hydrogen (1:1 molar). The reactor temperature was then raised to 195° C. and maintained at this temperature for two hours. When heating was started the pressure in the reactor rose above 120 bars. As soon as the reaction commenced the rate of increase in the pressure began to decrease. It was therefore necessary to make periodic injections of carbon monoxide and hydrogen (1:1 molar mixture) to compensate for the gas consumed by the reaction and maintain the rate of pressure increase in accord with achieving a pressure of 200 bars at 195° C. When the pressure reached 200 bars it was maintained at that value throughout the reaction by continually feeding fresh carbon monoxide and hydrogen (1:1 molar mixture) to the autoclave. After two hours at 195° C. the autoclave was allowed to cool and the reaction product was analysed. A single phase was observed at STP both before and after the reaction. The feed composition is given in Table 5A and the results are given in Table 6B.

Example 18

The procedure of Example 17 was followed except that a 1:2 molar carbon monoxide and hydrogen mixture was used instead of the 1:1 molar mixture. A single phase was observed at STP both before and after the reaction. The feed composition is given in Table 6A and the results are given in Table 6B.

It can be seen from Table 1B that the addition of an inert liquid (decanoic acid, silicone oil, chlorobenzene, tetrahydrothiophen or diphenylether) improves the realisable ethanol yield, decreases the yield of realisable acetic acid and improves the selectivity to realisable ethanol. Example 5 shows that the additional addition of water can further increase the realisable ethanol yield and selectivity.

Table 2B illustrates the effect of adding different quantities of inert liquid. Even small amounts of added inert liquid (eg molar ratio methanol:chlorobenzene=25:1) can improve the ethanol yield (Example 8), whilst larger quantities reduce the formation of realisable acetic acid (Example 2).

Table 3B shows the effect of varying the molar ratio of cobalt to tri-n-butylphosphine. The addition of tri-n-butylphosphine, even at the lowest concentration, leads to a marked improvement in realisable ethanol yield and selectivity.

Table 4B shows the effect of adding different compounds of formula I. It can be seen that the phosphorus-containing compounds are more effective than the nitrogen-containing compound.

Table 5B shows the additional advantage achievable by the addition of methyl acetate to the reactor feed ie the yield of the unwanted by product, realisable acetic acid is reduced.

Table 6B shows the additional advantage of using a 1:2 molar mixture of carbon monoxide and hydrogen instead of a 1:1 mixture. By so doing the yield of realisable acetic acid decreases giving an improved selectivity to ethanol.

TABLE 1A

EFFECT OF ADDING DIFFERENT TYPES OF INERT LIQUID

| | Reactor Feed | | | | | |
|---|---|---|---|---|---|---|
| | | Inert Liquid | | Catalyst Components | | |
| Example | $CH_3OH$ (moles) Nature | moles | No of (moles $\times 10^{-3}$) | Cobalt (moles $\times 10^{-3}$) | $I_2$ (moles $\times 10^{-3}$) | X(A)(B)(C) |
| (a) | (b) | (c) | (d) | (e) | (f) | (g) |
| Comp. | 2.0 | None | None | $Co(OAc)_2 4H_2O(25.0)$ | $I_2$ (12.5) | $P(C_4H_9)_3(43.7)$ |
| 1 | 0.68 | Silicone* Oil DC 200/ 100 cS | (55mls) | $Co(OAc)_2 4H_2O(8.4)$ | $I_2$ (4.2) | $P(C_4H_9)_3(14.8)$ |

TABLE 1A-continued
EFFECT OF ADDING DIFFERENT TYPES OF INERT LIQUID

| | Reactor Feed | | | | | |
|---|---|---|---|---|---|---|
| | $CH_3OH$ | Inert Liquid | | Catalyst Components | | |
| Example | (moles) | Nature | No of moles ($\times 10^{-3}$) | Cobalt (moles $\times 10^{-3}$) | $I_2$ (moles $\times 10^{-3}$) | X(A)(B)(C) |
| (a) | (b) | (c) | (d) | (e) | (f) | (g) |
| 2 | 0.80 | Chlorobenzene | 0.63 | $Co(OAc)_2 4H_2O(10.0)$ | $I_2$ (5.0) | $P(C_4H_9)_3(17.5)$ |
| 3 | 0.72 | Tetrahydrothiophen | 0.64 | $Co(OAc)_2 4H_2O(9.0)$ | $I_2$ (4.5) | $P(C_4H_9)_3(15.8)$ |
| 4 | 0.77 | Diphenyl ether | 0.39 | $Co(OAc)_2 4H_2O(9.6)$ | $I_2$ (4.8) | $P(C_4H_9)_3(16.8)$ |
| 5 | 0.80 + $H_2O$ 0.47 | Chlorobenzene | 0.63 | $Co(OAc)_2 4H_2O(10.0)$ | $I_2$ (5.0) | $P(C_4H_9)_3(17.3)$ |
| Comp Test B | 2.0 | None | None | $Co(OAc)_2 4H_2O(24.9)$ | $I_2$ (12.5) | $P(C_6H_{11})_3(46.8)$ |
| 6 | 4.41 | Decanoic acid | 0.66 | $Co(OAc)_2 4H_2O(55.1)$ | $I_2$ (27.4) | $P(C_6H_{11})_3(96.1)$ |

TABLE 2A
EFFECT OF VARYING THE AMOUNT OF ADDED INERT LIQUID

| (a) | (b) | (c) | (d) | (e) | (f) | (g) |
|---|---|---|---|---|---|---|
| 1 | 0.68 | Silicone* Oil DC 200/ 100 cS | (55mls) | $Co(OAc)_2 4H_2O(8.4)$ | $I_2$ (4.2) | $P(C_4H_9)_3(14.8)$ |
| 2 | 0.80 | Chlorobenzene | 0.63 | $Co(OAc)_2 4H_2O(10.0)$ | $I_2$ (5.0) | $P(C_4H_9)_3(17.5)$ |
| 7 | 1.66 | Chlorobenzene | 0.13 | $Co(OAc)_2 4H_2O(20.9)$ | $I_2$ (10.4) | $P(C_4H_9)_3(36.6)$ |
| 8 | 1.80 | Chlorobenzene | 0.072 | $Co(OAc)_2 4H_2O(22.5)$ | $I_2$ (11.3) | $P(C_4H_9)_3(39.3)$ |
| 9 | 1.80 | Silicone* Oil DC 200/ 100 cS | (7.3mls) | $Co(OAc)_2 4H_2O(22.5)$ | $I_2$ (11.3) | $P(C_4H_9)_3(39.3)$ |

*The amount of silicone oil added is quoted in mls because its molecular weight is not known.

TABLE 3A
EFFECT OF VARYING THE AMOUNT OF TRI-ALKYL PHOSPHINE

| (a) | (b) | (c) | (d) | (e) | (f) | (g) |
|---|---|---|---|---|---|---|
| 2 | 0.80 | Chlorobenzene | 0.63 | $Co(OAc)_2 4H_2O(10.0)$ | $I_2$ (5.0) | $P(C_4H_9)_3(17.5)$ |
| 10 | 0.80 | Chlorobenzene | 0.63 | $Co(OAc)_2 4H_2O(10.0)$ | $I_2$ (5.0) | $P(C_4H_9)_3(0.9)$ |
| 11 | 3.2 | Chlorobenzene | 2.52 | $Co(OAc)_2 4H_2O(40.0)$ | $I_2$ (20.0) | $P(C_4H_9)_3(20.0)$ |
| Comp Test C | 3.2 | Chlorobenzene | 2.52 | $Co(OAc)_2 4H_2O(40.0)$ | $I_2$ (20.0) | None |

TABLE 4A
EFFECT OF VARYING THE NATURE OF THE COMPOUND X(A)(B)(C)

| (a) | (b) | (c) | (d) | (e) | (f) | (g) |
|---|---|---|---|---|---|---|
| 2 | 0.80 | Chlorobenzene | 0.63 | $Co(OAc)_2 4H_2O(10.0)$ | $I_2$ (5.0) | $P(C_4H_9)_3(17.5)$ |
| 8 | 1.80 | Chlorobenzene | 0.072 | $Co(OAc)_2 4H_2O(22.5)$ | $I_2$ (11.3) | $P(C_4H_9)_3(39.3)$ |
| 12 | 1.78 | Chlorobenzene | 0.071 | $Co(OAc)_2 4H_2O(22.5)$ | $I_2$ (11.3) | $P(C_6H_5)_3(39.4)$ |
| 13 | 1.80 | Chlorobenzene | 0.072 | $Co(OAc)_2 4H_2O(22.5)$ | $I_2$ (11.3) | $N(C_6H_5)_3(39.4)$ |
| 14 | 0.80 | Chlorobenzene | 0.63 | $Co(OAc)_2 4H_2O(10.0)$ | $I_2$ (5.0) | $P(C_6H_5)_3(17.5)$ |
| 15 | 0.80 | Chlorobenzene | 0.63 | $Co(OAc)_2 4H_2O(10.0)$ | $I_2$ (5.0) | $P(C_6H_{11})_3(17.5)$ |

TABLE 5A
EFFECT OF ADDING COMPOUNDS ADDITIONAL TO THE INERT LIQUID

| (a) | (b) | (c) | (d) | (e) | (f) | (g) |
|---|---|---|---|---|---|---|
| 16 | 1.20 + methyl acetate 0.30 | Chlorobenzene | 0.060 | $Co(OAc)_2 4H_2O$(18.8) | $I_2$ (9.4) | $P(C_4H_9)_3$(32.8) |

TABLE 6A
EFFECT OF VARYING THE MOLAR RATIO OF CARBON MONOXIDE TO HYDROGEN

| (a) | (b) | (c) | (d) | (e) | (f) | (g) |
|---|---|---|---|---|---|---|
| 17 | 1.80 | Chlorobenzene | 0.072 | $Co(OAc)_2 4H_2O$(22.5) | $I_2$ (11.3) | $P(C_6H_5)_3$(39.3) |
| 18 | 1.80 | Chlorobenzene | 0.072 | $Co(OAc)_2 4H_2O$(22.5) | $I_2$ (11.3) | $P(C_6H_5)_3$(39.3) |

TABLE 1B
EFFECT OF ADDING DIFFERENT TYPES OF INERT LIQUID

| | % Molar yields on methanol fuel | | | | | | % Molar yield $CH_4$ +$CO_2$ *** | % Molar selectivity to realisable $C_2H_5OH$ | % $CH_3OH$ conversion |
|---|---|---|---|---|---|---|---|---|---|
| Example (h) | Realisable $C_2H_5OH$ (i) | Realisable $CH_3COOH$ (j) | Dimethyl acetal * (k) | $CH_3CHO$ (l) | Ethers ** (m) | n-$C_3H_7OH$ + n-$C_4H_9OH$ (n) | (o) | (p) | (q) |
| Comp Test A | 22.0 | 7.3 | 6.6 | <1 | 1.9 | 1.7 | 27.0 | 41.7 | 52.8 |
| 1 | 32.8 | 3.2 | 1.2 | 1.2 | <1 | <1 | 12.0 | 69.8 | 47.0 |
| 2 | 26.3 | 3.4 | 4.3 | <1 | 1.1 | <1 | 5.5 | 50.7 | 51.9 |
| 3 | 27.5 | 5.2 | 6.2 | <1 | <1 | <1 | 4.6 | 61.9 | 44.4 |
| 4 | 32.2 | 6.0 | 8.6 | 1.9 | 1.6 | 1.0 | 5.8 | 55.8 | 57.7 |
| 5 | 31.6 | 4.4 | 3.5 | <1 | <1 | <1 | 10.4 | 56.6 | 55.8 |
| Comp Test B | 12.9 | 10.9 | 3.9 | <1 | <1 | 1.0 | 10.7 | 34.5 | 37.4 |
| 6 | 26.5 | 6.6 | 2.9 | 1.5 | <1 | 1.7 | 9.9 | 53.0 | 50.0 |

* Dimethyl acetal is 1,1-dimethyoxy ethane
** Ethers are dimethyl ether + ethyl methyl ether
*** The % molar yield of methane plus carbon dioxide (ie $CH_4$ + $CO_2$) is calculated on the carbon monoxide fed to the reaction

TABLE 2B
EFFECT OF VARYING THE AMOUNT OF ADDED INERT LIQUID

| (h) | (i) | (j) | (k) | (l) | (m) | (n) | (o) | (p) | (q) |
|---|---|---|---|---|---|---|---|---|---|
| 1 | 32.8 | 3.2 | 1.2 | 1.2 | <1 | <1 | 12.0 | 69.8 | 47.0 |
| 2 | 26.3 | 3.4 | 4.3 | <1 | 1.1 | <1 | 5.5 | 50.7 | 51.9 |
| 7 | 29.0 | 6.6 | 5.3 | <1 | 1.1 | 1.6 | 16.0 | 48.3 | 60.0 |
| 8 | 28.8 | 6.9 | 6.4 | <1 | <1 | 2.2 | 19.6 | 47.8 | 60.3 |
| 9 | 25.8 | 7.8 | 4.8 | <1 | 1.1 | 1.7 | 20.7 | 53.9 | 47.9 |

TABLE 3B
EFFECT OF VARYING THE AMOUNT OF TRI-ALKYL PHOSPHINE

| (h) | (i) | (j) | (k) | (l) | (m) | (n) | (o) | (p) | (q) |
|---|---|---|---|---|---|---|---|---|---|
| 2 | 26.3 | 3.4 | 4.3 | <1 | 1.1 | <1 | 5.5 | 50.7 | 51.9 |
| 10 | 25.9 | 4.0 | 4.9 | <1 | <1 | 1.1 | 6.4 | 54.8 | 47.3 |
| 11 | 24.6 | 5.8 | 8.1 | <1 | 1.2 | <1 | 7.9 | 40.9 | 60.1 |
| Comp Test C | 14.4 | 7.2 | 19.9 | 1.9 | 7.2 | <1 | 7.5 | 20.8 | 69.2 |

TABLE 4B
EFFECT OF VARYING THE NATURE OF THE COMPOUND X(A)(B)(C)

| (h) | (i) | (j) | (k) | (l) | (m) | (n) | (o) | (p) | (q) |
|---|---|---|---|---|---|---|---|---|---|
| 2 | 26.3 | 3.4 | 4.3 | <1 | 1.1 | <1 | 5.5 | 50.7 | 51.9 |
| 8 | 28.8 | 6.9 | 6.4 | <1 | <1 | 2.2 | 19.6 | 47.8 | 60.3 |
| 12 | 29.0 | 10.1 | 3.5 | 1.3 | <1 | 2.5 | 9.3 | 44.8 | 64.8 |
| 13 | 19.8 | 12.7 | 2.8 | 1.1 | <1 | 2.1 | 16.3 | 36.7 | 53.9 |
| 14 | 28.2 | 5.7 | 9.4 | <1 | 1.2 | 1.0 | 6.9 | 44.4 | 63.5 |
| 15 | 20.5 | 3.6 | 6.5 | <1 | <1 | <1 | 4.7 | 53.1 | 38.6 |

TABLE 5B
EFFECT OF ADDING COMPOUNDS ADDITIONAL TO THE INERT LIQUID

| (h) | (i) | (j) | (k) | (l) | (m) | (n) | (o) | (p) | (q) |
|---|---|---|---|---|---|---|---|---|---|
| 16 | 28.0 | 3.4 | 3.8 | 2.0 | 1.3 | 1.1 | 10.5 | 55.3 | 50.6 |

TABLE 6B
EFFECT OF VARYING THE MOLAR RATIO OF CARBON MONOXIDE TO HYDROGEN

| (h) | (i) | (j) | (k) | (l) | (m) | (n) | (o) | (p) | (q) |
|---|---|---|---|---|---|---|---|---|---|
| 17 | 31.2 | 11.7 | 6.7 | 3.2 | <1 | 3.0 | 10.0 | 42.1 | 74.1 |
| 18 | 28.1 | 3.1 | 6.8 | 1.7 | <1 | 1.9 | 6.7 | 58.4 | 48.1 |

We claim:

1. A process for the production of ethanol which process comprises reacting, at elevated temperature and pressure, methanol with hydrogen and carbon monoxide in the presence of an aryl halide, a thiophene, or a silicone oil inert liquid which is deliberately charged to the reaction system, and a catalyst comprising cobalt, an iodide or a bromide and a compound having the formula

wherein X is nitrogen or phosphorus and A, B, and C are individually monovalent organic radicals, or X is phosphorus and any two of A, B, and C together form an organic divalent cyclic ring system bonded to the X atom, or X is nitrogen and all of A, B and C together form an organic trivalent cyclic ring system bonded to the X atom.

2. A process according to claim 1 wherein the elevated temperature is in the range 150° to 250° C., the elevated pressure is greater than 100 bars, the residence time is up to 8 hours, the molar ratio of carbon monoxide to hydrogen is in the range 2:1 to 1:3, the molar ratio of methanol to inert liquid is in the range from 30:1 to 1:10, the molar ratio of methanol to synthesis gas is in the range from 10:1 to 1:20, the molar ratio of cobalt to iodine or bromine in the catalyst is in the range from 1:3 to 10:1, the molar ratio of cobalt to the compound of formula (I) in the catalyst is in the range from 2:1 to 1:10, the molar ratio of iodine or bromine to the compound of formula (I) in the catalyst is in the range from 2:1 to 1:10 and the molar ratio of cobalt to methanol is in the range from 1:10 to 1:1000.

3. A process according to claim 1 wherein the elevated temperature is in the range from 180° to 230° C., the elevated pressure is in the range 140 to 300 bars, the residence time is from 10 to 180 minutes, the molar ratio of carbon monoxide to hydrogen is in the range 2:1 to 1:3, the molar ratio of methanol to inert liquid is in the range from 25:1 to 1:2, the molar ratio of methanol to synthesis gas is in the range from 2:1 to 1:5, the molar ratio of cobalt to iodine in the catalyst is in the range from 1:1 to 5:1, the molar ratio of cobalt to the compound of formula (I) in the catalyst is in the range from 1:1 to 1:5, the molar ratio of iodine or bromine to the compound of formula (I) in the catalyst is in the range from 1:1 to 1:8 and the molar ratio of cobalt to methanol is in the range from 1:40 to 1:800.

4. A process according to claim 1 wherein the molar ratio of carbon monoxide to hydrogen is in the range 1:1 to 1:2.

5. A process according to claim 1 wherein the compound having the formula (I) is a phosphine having the general formula:

$$R_3P \qquad (II)$$

wherein R independently is a hydrocarbyl group containing from 1 to 20 carbon atoms selected from unsubstituted saturated aliphatic, unsubstituted saturated cycloaliphatic and unsubstituted aromatic groups.

6. A process according to claim 5 wherein the phosphine of formula (II) is triethyl phosphine, tributyl phosphine, tri-t-butyl phosphine or triphenylphosphine.

7. A process according to claim 1 wherein the compound of formula (I) is pyridine or diphenylamine.

8. A process according to claim 1 wherein, in addition to the inert liquid, there is added a nonpolar solvent selected from alkanes, benzene and alkyl-substituted benzenes.

9. A process according to claim 1 wherein, in addition to the inert liquid, there is added an acid and/or an acid derivative thereof having the formula:

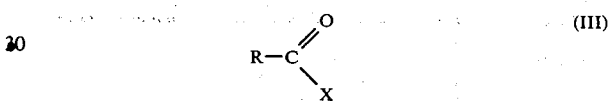

wherein the substituent R is a hydrocarbyl group or an oxygen-containing hydrocarbyl group and the substituent X is the group —OR$^1$ in which R$^1$ is independently a hydrogen atom, a hydrocarbyl group or an oxygen-containing hydrocarbyl group or X is the group —O—CO—R$^2$ in which R$^2$ is independently a hydrocarbyl group or an oxygen-containing hydrocarbyl group.

10. A process according to claim 1 when operated in a continuous manner.

11. A process as defined in claim 1 wherein said inert liquid is a chlorobenzene, tetrahydrothiophene, a polydimethyl siloxane fluid or a methyl phenyl silicone fluid.

* * * * *

UNITED STATES PATENT AND TRADEMARK OFFICE
CERTIFICATE OF CORRECTION

PATENT NO. : 4,319,056

DATED : March 9, 1982

INVENTOR(S) : Brian R. Gane and David G. Stewart

It is certified that error appears in the above-identified patent and that said Letters Patent is hereby corrected as shown below:

Col. 1, line 64, insert --now-- after "have" and before "found".

Col. 3, line 42, after "Specific" and before "fluids" insert --silicone--.

Cols. 9 and 10, also repeated at Cols. 11 and 12, correct the "Table 1A" headings as follows:

Delete "Nature" in heading above col. "(b)".
Delete "moles" in heading above col. "(c)", and insert --Nature-- in lieu thereof.
Delete "(moles x $10^{-3}$" in heading above col. "(d)", and insert --moles-- in lieu thereof.
In heading above "(g)", "X(A)(B)(C)" should read --X(A)(B)(C)$_3$--; and insert --(moles x $10^{-3}$) thereunder.

Cols. 9 and 10, in col. "(a)" under "Example", "Comp." should read --Comp
            Test A--

UNITED STATES PATENT AND TRADEMARK OFFICE
CERTIFICATE OF CORRECTION

PATENT NO. : 4,319,056  
DATED : March 9, 1982  
INVENTOR(S) : BRIAN R. GANE and DAVID G. STEWART Page 2 of 2

It is certified that error appears in the above—identified patent and that said Letters Patent is hereby corrected as shown below:

Cols. 11 and 12, Table 3A, Example 10, under heading "(g)", "$P(C_4H_9)_3(0.9)$" should read --$P(C_4H_9)_3(8.9)$--.

Cols. 13 and 14, Table 1B, in the heading "% Molar yields on methanol fuel", delete "fuel" and insert --fed-- in lieu thereof.

Col. 14, Table 5B, under the heading "(o)", delete "10.5" and insert --10.6-- in lieu thereof.

Signed and Sealed this

Fifteenth Day of March 1983

[SEAL]

Attest:

GERALD J. MOSSINGHOFF

Attesting Officer Commissioner of Patents and Trademarks